(12) United States Patent
Antonini et al.

(10) Patent No.: US 8,298,786 B2
(45) Date of Patent: Oct. 30, 2012

(54) COLORIMETRIC METHOD AND RELATIVE DEVICE FOR BACTERIAL LOAD DETECTION

(75) Inventors: Giovanni Antonini, Rome (IT); Alberto Mari, Rome (IT); Maria Teresa Massucci, Raiano (IT)

(73) Assignee: M.B.S. S.R.L., Rome (IT)

( * ) Notice: Subject to any disclaimer, the term of this patent is extended or adjusted under 35 U.S.C. 154(b) by 513 days.

(21) Appl. No.: 12/373,102

(22) PCT Filed: Jul. 10, 2007

(86) PCT No.: PCT/IB2007/001926
§ 371 (c)(1),
(2), (4) Date: May 28, 2009

(87) PCT Pub. No.: WO2008/007206
PCT Pub. Date: Jan. 17, 2008

(65) Prior Publication Data
US 2009/0311740 A1    Dec. 17, 2009

(30) Foreign Application Priority Data
Jul. 11, 2006  (IT) .............................. BO2006A0531

(51) Int. Cl.
*C12Q 1/06* (2006.01)
*C12Q 1/04* (2006.01)
(52) U.S. Cl. .......................................... 435/39; 435/34
(58) Field of Classification Search .................. None
See application file for complete search history.

(56) References Cited

U.S. PATENT DOCUMENTS

| | | | |
|---|---|---|---|
| 3,936,356 A | 2/1976 | Janin | |
| 4,235,964 A | 11/1980 | Bochner | |
| 5,091,307 A * | 2/1992 | Escarguel et al. | 435/34 |
| 6,543,495 B2 * | 4/2003 | Hougland | 141/234 |

FOREIGN PATENT DOCUMENTS

| | | |
|---|---|---|
| EP | 0 509 791 A1 | 10/1992 |
| WO | 96/28570 | 9/1996 |

OTHER PUBLICATIONS

Difco Manual. 11th Edition, 1999, pp. 358-359.*
Gernhardt et al. In: "Manual of Methods for General Bacteriology"; 1981, pp. 420, 421, 433-435, 487-488.*

* cited by examiner

*Primary Examiner* — Vera Afremova
(74) *Attorney, Agent, or Firm* — Workman Nydegger

(57) ABSTRACT

A method for detecting a bacterial load comprising adding a sample for analysis to an analysis reagent in a sterilized reaction container, thermostatting the reaction container at a temperature of between 25 and 45° C., and verifying the change in colouring of the analysis reagent. The analysis reagent is an aqueous solution comprising amino acids chosen from the group consisting of meat peptones, vegetable peptones, casein hydrolysates, tryptose, tryptones and yeast extract; glucides chosen from monometric or oligomeric glucides metabolisable by micro-organisms; a buffer system suitable for maintaining the pH between 5.5 and 8.5; a redox indicator with potential between −250 and +250 mV and/or a pH indicator with colour change interval between pH 4.0 and pH 9.0; and a water-immiscible organic liquid compound having a lower density than water and suitable for separating the aqueous phase from a gaseous phase existing prior to the analysis or formed during the reaction.

15 Claims, 4 Drawing Sheets

COLORIMETRIC METHOD AND RELATIVE DEVICE FOR BACTERIAL LOAD DETECTION

TECHNICAL FIELD

The present invention concerns a calorimetric method and relative device for bacterial load detection.

BACKGROUND ART

In the food sector it is becoming increasingly necessary to guarantee greater safety in terms of hygiene and health of food and water.

Both high technology countries and the developing countries, for different reasons, require simple, rapid and inexpensive microbiological control of food and water. So far no microbiological analysis methods with characteristics combining simplicity of use, rapidity of analysis and low cost are available on the market.

Food and water analysis most frequently involves identification of the so-called "indicators", i.e. micro-organisms which, when absent, provide a reliable indication of the absence of pathogenic micro-organisms. Among the "indicators", the most important is the quantitative search for total micro-organisms, coliforms/*E. coli* and coagulase-positive staphylococci (*St. aureus*). The detection of such micro-organisms covers approximately 40-50% of the microbiological analyses in the water and food sector.

The traditional method for detection of micro-organisms present in a liquid (e.g. water) or in a solid (foodstuffs) is based on microbial multiplication detection. In fact micro-organisms, normally invisible to the naked eye, can be detected when, as a result of multiplication by successive divisions from a single cell (clones), aggregates of billions of cells (colonies) form, visible to the naked eye. The traditional methods based on bacterial multiplication are therefore also called Colony-Forming Unit (CFU) count. Specific detection of a particular type of micro-organism is ensured by the use of selective nutritional media. The multiplication of the micro-organisms can be easily observed by the naked eye in selective media, both solid (plate count method for microbiological examination of liquids) and liquid (method of the "most probable number" for the microbiological examination of solids). In the plate count method, the solid selective media in general are contained in transparent capsules. One drop of the liquid sample to be examined (concentrated on filters if necessary) is deposited on the selective nutritional medium and multiplication of the micro-organisms becomes visible in the form of "colonies", each formed of billions of cells, all deriving from at least 20-22 successive divisions of one single cell (clones). These clones appear as small protuberances with dimensions from 0.5 to 1 mm or more. From the number of colonies present in one single capsule, the number of micro-organisms initially present in the drop of liquid sample deposited on the nutritional medium can therefore be traced.

In the method of the "most probable number" the liquid selective media are contained in transparent test tubes. A small homogenised quantity of the solid sample to be examined is added to these test tubes. Multiplication of the micro-organisms is indicated by the appearance of a widespread cloudiness of the nutritional medium contained in the test tube. By means of tables drawn up on a statistical basis, the "most probable number" of micro-organisms initially present in the solid sample can be traced according to the presence or absence of the cloudiness in the different test tubes at different dilutions of the sample to be examined.

It is evident from the above that these methods are demanding in terms of the work process and require the presence of an equipped laboratory in order to previously sterilise the material to be used and maintain it in sterile conditions. The absence of sterility would lead to microbial contamination from outside the sample, thus rendering the analysis performed meaningless.

Alternative methods are currently used, such as the one based on the use of chromogenic media. Although this too is a cultivation method, the use of chromogenic media for the microbiological analysis can often be considered a "rapid" method, as it permits optimisation of the search for specific micro-organisms without the need to perform sub-cultures and sometimes even without the need for confirmation tests.

Of the rapid methods, the use of antibodies is the one with the greatest impact in the food sector. The specificity of the monoclonal antibodies, the simplicity and versatility of the antigen-antibody reaction has permitted the development of numerous immunological analysis methods. These methods, however, suffer from the drawbacks relative to the need for specialist personnel and equipment, and the high sensitivity level of at least $10^4$ cells/ml.

Lastly, genetic molecular analysis methods have been used more recently. These methods comprise DNA/DNA hybridisation, analyses of the rRNA (ribosomal RNA) sequences, use of oligonucleotide probes complementary to the rRNA or to other target genes, ribotypification and PCR-Polymerase Chain Reaction. These methods, although they have the advantage of a low sensitivity limit ($<10^2$ cells/ml), do not solve the problem of the need for highly specialised personnel for the use of complex equipment, controlled environments to prevent contamination of the sample and, furthermore, are often not able to distinguish between living or dead micro-organisms.

DISCLOSURE OF INVENTION

The aim of the present invention is to devise a process for the detection of bacterial load, the technical characteristics of which are such as to make it efficient, economic and, at the same time, easy to use without requiring the intervention of specialist personnel.

The subject of the present invention is a method for bacterial load detection comprising the phases of adding a sample to be analysed to an analysis reagent in a suitable reaction container appropriately sterilised, of thermostatting said reaction container at a temperature between 25 and 45° C. and of verifying the colour change of said analysis reagent; said method being characterised in that said analysis reagent is an aqueous solution comprising from 1 to 100 g/l of a source of amino acids chosen from the group consisting of meat peptones, vegetable peptones, casein hydrolysates, tryptose, tryptones and yeast extract; from 0 to 50 g/l of a source of glucides chosen from monometric or oligomeric glucides metabolisable by the micro-organisms; from 0 to 200 g/l of a buffer system suitable for maintaining the overall pH between 5.5 and 8.5; from 0.03 to 3 g/l of a redox indicator with potential between −250 and +250 mV and/or a pH indicator with colour change interval between pH 4.0 and pH 9.0; and an organic liquid compound not miscible with the water and with lower density than the water itself and suitable for separating the aqueous phase from a gaseous phase existing prior to the analysis or formed during the reaction.

Preferably, the colour change verification phase comprises illuminating the sample on at least two different wavelengths in the range between 500 and 700 nm and reception of the reflected and/or transmitted radiation.

Preferably, verification of the colour change comprises calculation of the time necessary for said analysis reagent to change colour.

Preferably, the analysis reagent comprises from 0 to 200 g/l of a selective agent for the detection of a specific class of bacteria.

Preferably, the method of the present invention comprises a final sterilisation phase in which, once the analysis has been completed, a sterilising substance is added to the reaction container.

Preferably, said reaction container is a disposable vial comprising a container portion made of transparent material and a stopper suitable for coupling with the container portion by means of respective threads, and comprising a reservoir housing the sterilising substance and suitable for being emptied into the container portion by means of a pressure shearing action.

A further subject of the present invention is an analysis device for realisation of the method according to one of the preceding claims, comprising at least one analysis unit and one central command/control unit connected to said analysis unit to command/control operation thereof and receive information on the basis of which to calculate the bacterial concentration by comparison with previously set parameters; said analysis unit comprising an analysis cavity coated in a layer of reflecting material and suitable for housing an analysis container in which the sample for analysis is deposited, a thermostat suitable for maintaining said analysis cavity at a temperature between 25 and 45° C., means for emitting radiation inside said analysis cavity and a radiation receiver element in said analysis cavity; said device being characterised in that said emitter means emit into said analysis cavity on at least two different wavelengths in the range 500-700 nm.

Preferably, the emitter means and the receiver element are located in the analysis cavity at the same height, and in a position such as to be spaced from one another by an angle less than or equal to 90°.

Preferably, the emitter means emit on at least three different wavelengths in the range 500-700 nm.

Preferably, the device of the present invention comprises a plurality of analysis units.

Preferably, the device of the present invention comprises means for display of the results obtained by the central command/control unit.

BRIEF DESCRIPTION OF THE DRAWINGS

The following examples are provided for illustrative non-limiting purposes, for a better understanding of the invention with the help of the figures of the accompanying drawing, in which.

BEST MODE FOR CARRYING OUT THE INVENTION

Figure 1:
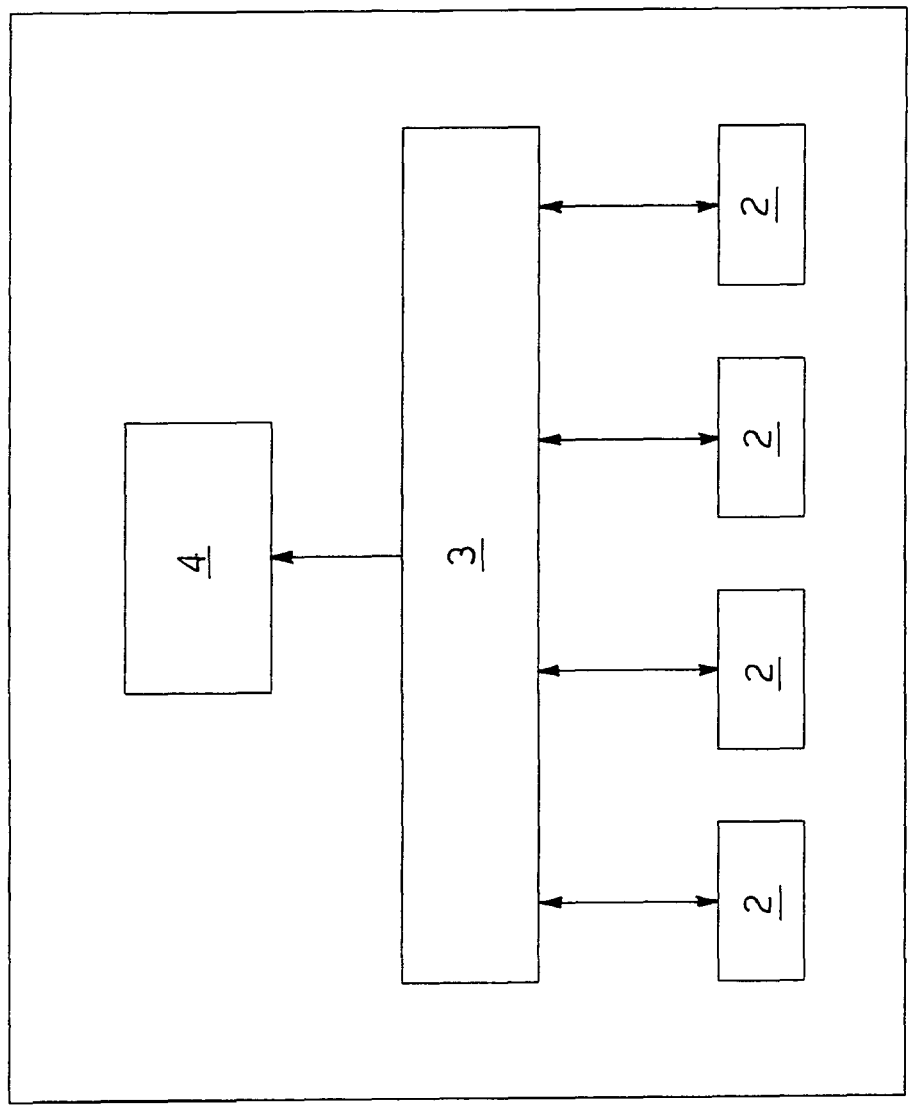
FIG. 1 schematically illustrates the device subject of the present invention.

In FIG. 1, 1 indicates overall the analysis device according to the present invention. The device 1 comprises a plurality of analysis units 2, a central command/control unit 3 and means for display 4 of the results obtained.

Figure 2:
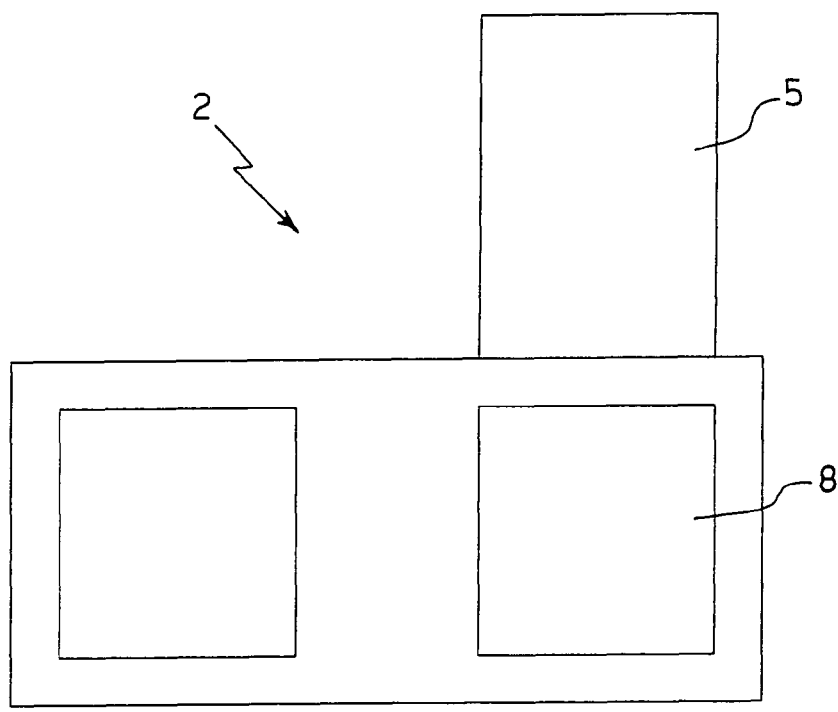
FIG. 2 is a lateral schematic view of the analysis unit of the device according to a preferred embodiment.
Figure 3:
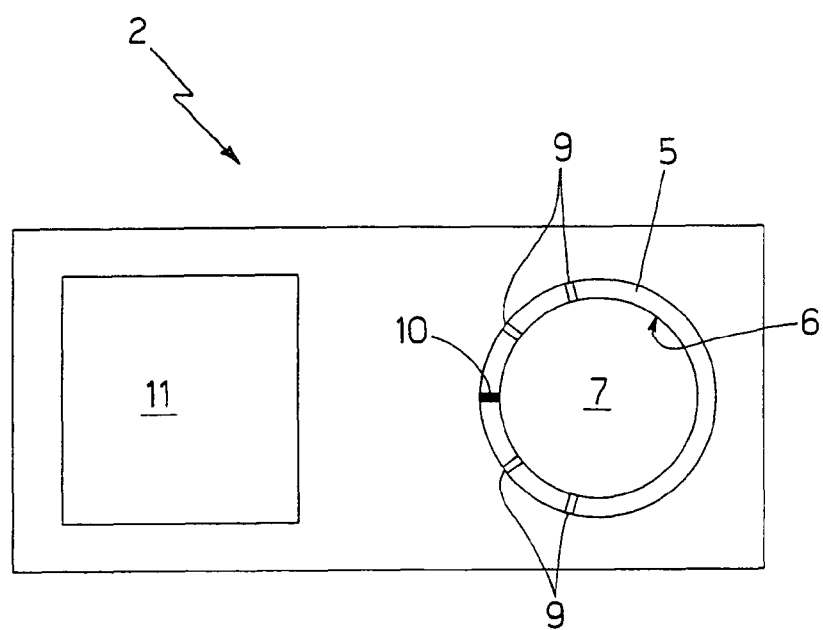
FIG. 3 is a schematic plan view of the analysis unit of FIG. 1.

As illustrated schematically in FIGS. 2 and 3, each of the analysis units 2 comprises a cylindrical wall 5 lined with a layer of reflecting material 6, and defining an analysis cavity 7 housing a vial in which the sample for analysis is made to react with the reagent of the present invention. The analysis unit 2 comprises, furthermore, a thermostat illustrated schematically by 8, suitable for maintaining the analysis cavity 7 at a temperature between 25 and 45° C., four emitter LEDs 9, two of which emit at 560 nm and two emit at 660 nm, a high performance visible light receiver photodiode 10, and an electric circuit for powering and amplifying the signal indicated schematically by 11. The use of at least two wavelengths permits evaluation of the colour change even when the reagent solution plus the sample is cloudy. In this way it is possible to perform alternate reading on at least two wavelengths and subtraction of the aspecific absorption due to the cloudiness of the sample to determine the colour change.

The relative position of the receiver photodiode 10 and the emitter LEDs 9 permits detection of the radiation both according to the phenomenon of reflectance and according to the phenomenon of transmittance, consequently guaranteeing greater detection efficiency.

Figure 4:
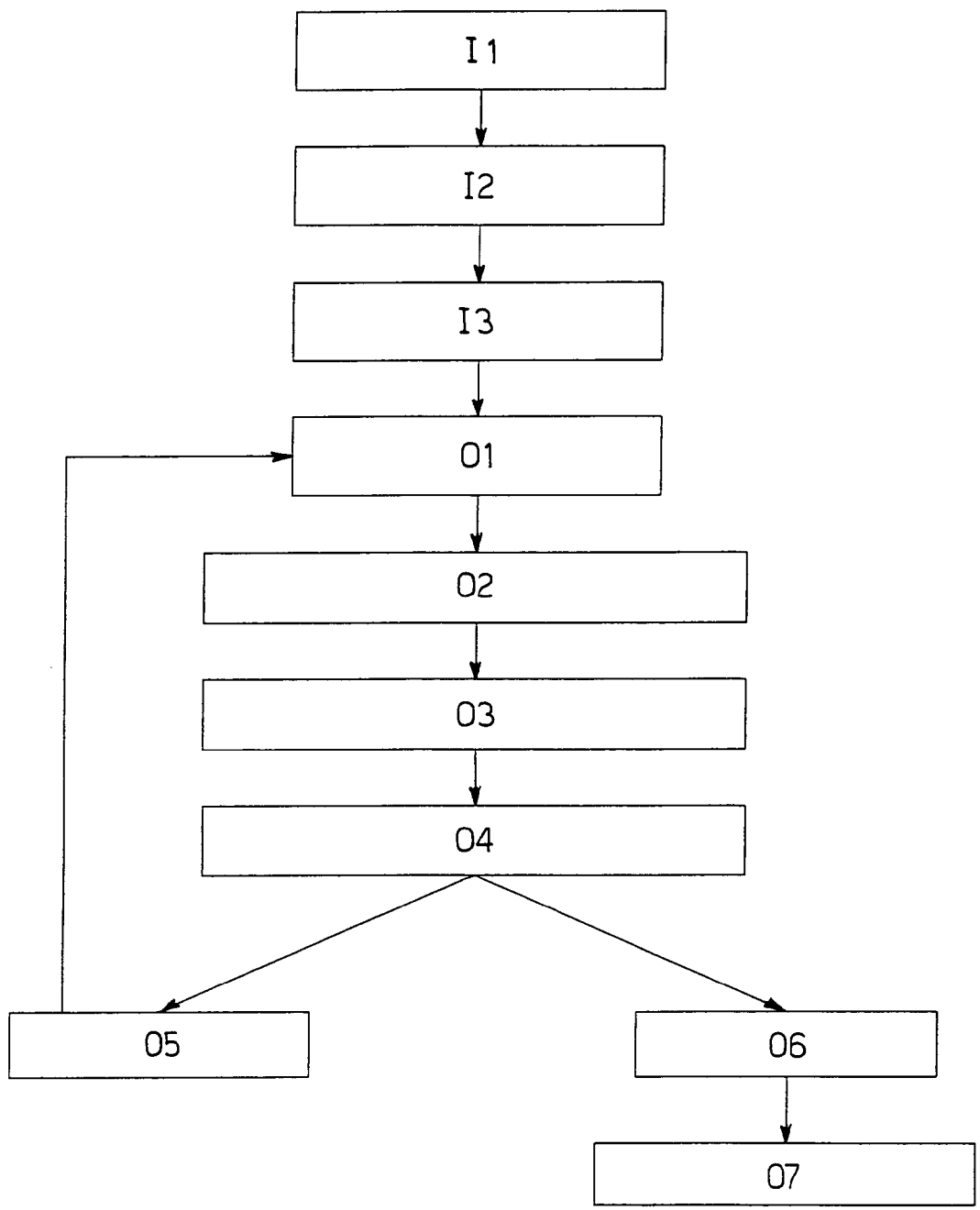
FIG. 4 is a flow chart illustrating the operations performed by the central command/control unit of the device of the present invention.

FIG. 4 shows the block diagram relative to the settings to be communicated to the central unit 3 and the operations to be performed by the same.

In particular, the central command/control unit 3 constitutes the interface of the device with the operator and is connected to the thermostat 8, to the emitter LEDs 9 and to the receiver photodiode 10.

With reference to the block diagram of FIG. 4, the housing of the vials indicated by I1, the choice of the type of analysis indicated by I2 and the start of the analysis indicated by I3 must be set in the central unit 3. Subsequently, the operations performed by the central unit 3 are: the command to the unit 2 for illuminating the sample by means of the LEDs 9 indicated by O1, reading of the luminous intensity by means of the receiver photodiode 10 indicated by O2, calculation of the specific absorption indicated by O3 and comparison with the absorption at time zero indicated by O4. If the operation O4 results in absence of colour change, the central unit communicates the absence of bacterial load (operation indicated by O5) via the display means 4, whereas if the operation O4 results in colour change, the central unit 3 calculates the concentration of the bacterial load (operation indicated by O6) and communicates the result (operation indicated by O7) via the display means 4.

The operation O6 is based on the demonstrated correlation between the number of bacteria present in the sample and the time necessary for the colour change of the reagent. On the basis of this correlation, specific calibration lines have been realised for the different bacterial strains, relating the logarithm of the concentration of the bacteria present in the sample to the time necessary for colour change of the reagent. The data of said lines are set in the central unit 3 and used by comparison in operation O6 with the findings of operation O4.

Figure 5:
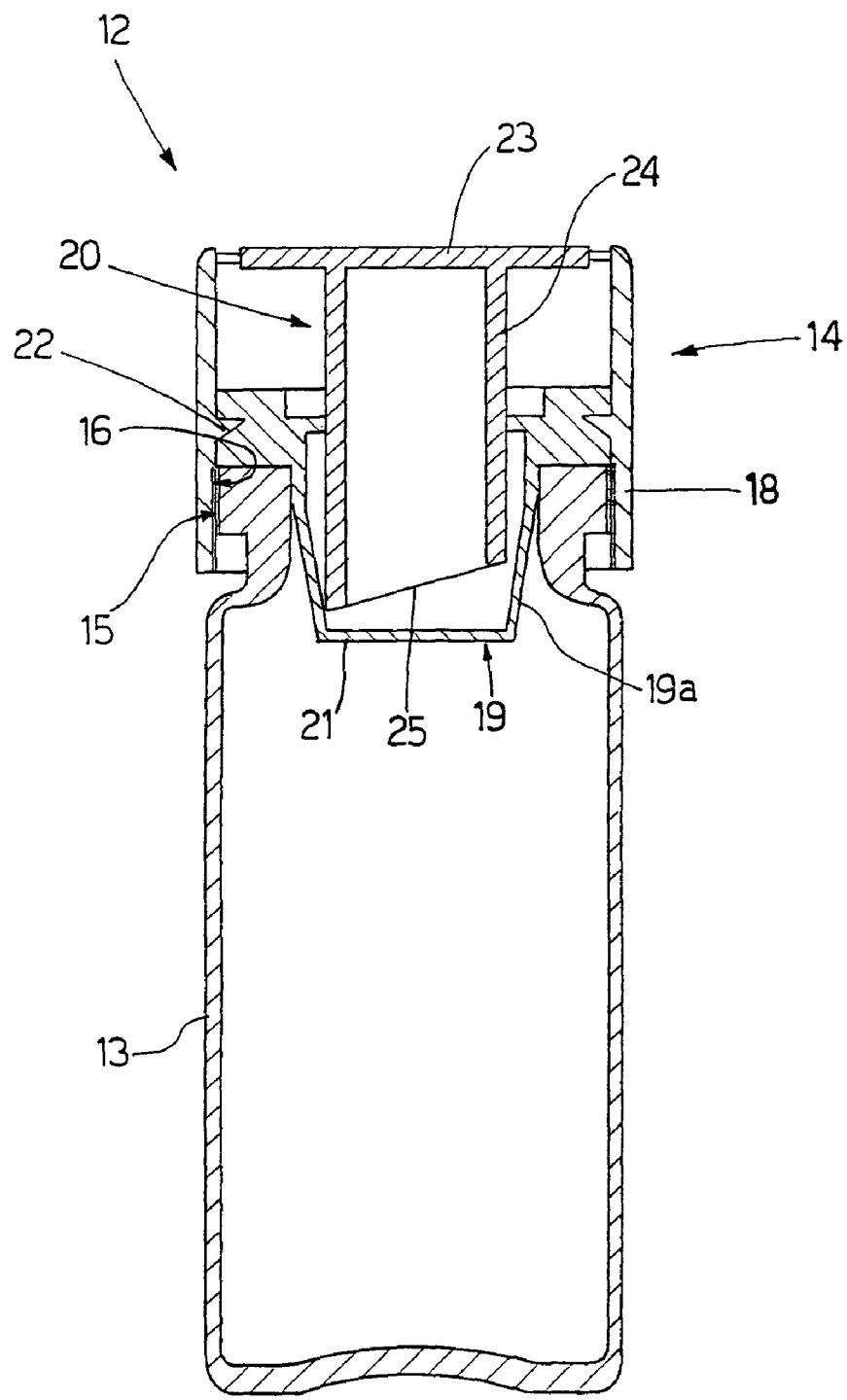
FIG. 5 is a section of a vial according to the present invention.

In FIG. 5 a vial used in the method of the present invention is indicated overall by 12. The vial 12 comprises a container portion 13 made of transparent material, and a stopper 14 suitable for closing or opening the container portion 13. Both the container portion 13 and the stopper 14 are provided with thread, indicated by 15 and 16 respectively, for coupling or release by means of a screwing or unscrewing action respectively.

The stopper 14 comprises a lateral wall 18 of cylindrical shape in which the thread 16 is obtained, a reservoir stopper 19 fixed to the lateral wall 18, and a shearing stopper 20 containing the sterilising substance and suitable for running inside the lateral wall 18 to permit shearing of a membrane 21 at the bottom of the reservoir stopper 19 and consequent discharge of the sterilising substance inside the container portion 13.

The reservoir stopper 19 comprises a cup-shaped body 19a fixed to the lateral wall 18 by the action of a peripheral lock tooth 22 extending from the lateral wall 18 itself.

The shearing stopper 20 comprises an activator head 23 which the operator presses, and a cylindrical wall 24 having a shearing end 25 suitable for shearing the membrane 21 at the bottom of the cup-shaped body 19a.

In other words, to deposit the sterilising substance in the container portion 13, the operator must exert a pressure on the activator head 23 causing shearing of the membrane 21 at the bottom by the shearing end 25 and consequent outflow of the sterilising substance. In this regard it should be specified that the preferred sterilising substance is dichloroisocyanide.

The presence of the threads 15 and 16 guarantees a practical opening and closing action of the container portion 13 by the stopper 14, and at the same time prevents accidental opening when the stopper 14 is tightened.

The vial has a working volume of approximately 13 ml, and contains the reagent in a quantity varying between 1 and 2 g which, when the analysis is performed, will be added to 10 ml of liquid sample or to 0.1-1 g of solid sample with the addition of 9-10 ml of sterile deionised water. The vials as described above can be sold ready for use and, therefore, already sterilised and containing the reagent for the analysis.

Below four examples of reagent of the present invention are given. In particular, the reagent 1 is aspecific and can be used to detect all bacteria with the exception of the obligatory anaerobic bacteria, the reagent 2 is specific for the species *Staphylococcus*, the reagent 3 is specific for the enterobacteriaceae, and the reagent 4 is specific for the coliforms.

REAGENT 1 CBT (1.24 g per 13 ml vial)

| Type of component | Component | g/l |
|---|---|---|
| Source of amino acids | Brain heart infusion | 10 |
| Source of amino acids | Yeast extract | 1 |
| Buffer system | HEPES * | 10 |
| Buffer system | TRIS ** | 2.5 |
| Indicator | TMPD *** | 0.25 |
| Organic liquid | White mineral oil | 100 ml |

REAGENT 2 *Stsaphylococcus aureus* (1.85 g per 13 ml vial)

| Type of component | Component | g/l |
|---|---|---|
| Source of amino acids | Brain heart infusion | 20 |
| Source of glucides | Mannitol | 10 |
| Selective agent | Polymyxin B | 0.3 |
| Selective agent | NaCl | 50 |
| Buffer system | $K_2HPO_4$ | 5 |
| Indicator | Phenol red | 0.3 |
| Indicator | TMPD *** | 0.25 |
| Organic liquid | White mineral oil | 100 ml |

REAGENT 3 Enterobacteria (1.53 g per 13 ml vial)

| Type of component | Component | g/l |
|---|---|---|
| Source of amino acids | Brain heart infusion | 20 |
| Source of glucides | Glucose | 10 |
| Selective agent | Sodium cholate | 10 |
| Buffer system | HEPES * | 10 |
| Buffer system | TRIS ** | 2.5 |
| Indicator | TMPD *** | 0.25 |
| Organic liquid | White mineral oil | 100 ml |

REAGENT 4 Coli (1.53 g per 13 ml vial)

| Type of component | Component | g/l |
|---|---|---|
| Source of amino acids | Brain heart infusion | 20 |
| Source of glucides | Lactose | 10 |
| Selective agent | Sodium cholate | 10 |
| Selective agent | Tryptophan | 0.07 |
| Buffer system | HEPES * | 10 |
| Buffer system | TRIS ** | 2.5 |
| Indicator | Phenol red | 0.3 |
| Indicator | TMPD *** | 0.25 |
| Organic liquid | White mineral oil | 100 ml |

* HEPES: 4-(2-hydroxyethyl)-1-piperazineethanesulphonic acid
** TRIS: tris(hydroxymethyl)aminoethane
*** TMPD: N,N,N'N'-tetramethyl-p-phenylenediamine hydrochloride (N,N,N',N'-tetramethyl benzene-1,4-diamine hydrochloride)

As will be obvious to a person skilled in the art, the compositions of the reagents 1-4 constitute the best embodiments in relation to the types of bacteria mentioned. The present invention, however, relates to the compositions of the reagents as claimed.

The invention claimed is:
1. A method for the detection of bacterial load, the method comprising:
adding a sample to be analysed to an analysis reagent in a suitable reaction container that is appropriately sterilised, wherein the reaction container is at a temperature between about 25 and about 45° C.;
verifying a colour change of the analysis reagent; and once the verifying has been completed, adding a sterilising substance in the reaction container without opening the reaction container;
wherein the analysis reagent is an aqueous solution comprising:
from about 1 to about 100 g/l of at least one source of amino acids chosen from the group consisting of meat peptones, vegetable peptones, casein hydrolysates, tryptose, tryptones, and yeast extract;
from about 0 to about 200 g/l of a buffer system suitable for maintaining the overall pH between about 5.5 and about 8.5;
from about 0.03 to about 3 g/l of a redox indicator with a potential between about −250 and about +250 mV;
a pH indicator with a colour change interval between a pH of about 5.5 and a pH of about 8.5;
from about 0 to about 200 g/l of a selective agent for the detection of a specific class of bacteria; and
an organic liquid compound that is not miscible with water and having a lower density than water and suitable for separating an aqueous phase from a gaseous phase existing prior to the verifying or formed during a reaction between the sample and the analysis reagent;

calculating a time for the colour change to occur; and determining a concentration of the bacteria load present in the sample at least partially based on the time.

2. The method according to claim 1, wherein the analysis reagent comprises at least one source of glucides chosen from the group consisting of monometric glucides metabolisable by the bacteria and oligomeric glucides metabolisable by the bacteria.

3. The method according to claim 1, wherein verifying a colour change comprises calculating a time necessary for occurrence of the colour change of the analysis reagent.

4. The method according to claim 1, wherein said reaction container is a disposable vial containing the analysis reagent and comprising a container portion made of a substantially transparent material and a stopper which can be coupled to each other by respective threads; the stopper comprising a reservoir housing the sterilising substance suitable for being emptied into the container portion by a pressure shearing action.

5. The method according to claim 4, wherein the stopper comprises a lateral wall having a generally cylindrical shape in which the thread is obtained, a reservoir stopper fixed to the lateral wall, and a shearing stopper suitable for running inside the lateral wall to permit shearing of a bottom membrane of the reservoir stopper and consequent discharge of the sterilising substance inside the container portion.

6. The method of claim 1, wherein verifying a colour change of the analysis reagent comprises illuminating the sample with radiation.

7. The method of claim 6, further comprising receiving reflected and/or transmitted radiation in response to illuminating the sample with the radiation.

8. A method for detecting bacteria, comprising:

adding a sample, to be analysed, to an analysis reagent held in a reaction container, wherein the reaction container is appropriately sterilised and maintained at a temperature of about 25 to about 45° C.;

detecting a colour change of the analysis reagent in response to adding the sample to the analysis reagent;

wherein the analysis reagent includes an aqueous solution including:

about 1 to about 100 g/l of at least one source of amino acids selected from the group consisting of meat peptone, vegetable peptone, casein hydrolysate, tryptose, tryptone, and yeast extract;

about 0 to about 200 g/l of a buffer system suitable for maintaining the overall pH between about 5.5 and about 8.5;

about 0.03 to about 3 g/l of a redox indicator having a potential between about −250 and about +250 mV;

a pH indicator with a colour change interval between a pH of about 5.5 and a pH of about 8.5;

about 0 to about 200 g/l of a selective agent for the detection of a specific class of bacteria; and an organic liquid compound that is not miscible with water and has a density less than water;

calculating a time for the colour change to occur; and determining a concentration of the bacteria present in the sample at least partially based on the time.

9. The method of claim 8, wherein verifying a colour change of the analysis reagent comprises illuminating the sample with radiation.

10. The method of claim 9, further comprising receiving reflected and/or transmitted radiation in response to illuminating the sample with the radiation.

11. The method of claim 9, wherein illuminating the sample with radiation comprises illuminating the sample radiation having at least two different wavelengths of about 500 nm to about 700 nm.

12. The method of claim 9, further comprising adding a sterilisation substance to the reaction container without opening the reaction container.

13. The method of claim 9, further comprising determining a concentration of bacteria present in the sample at least partially based on a time for the colour change to occur.

14. The method of claim 8, wherein determining a concentration of bacteria present in the sample at least partially based on a time for the colour change to occur is at least partially based on a correlation between the time for the colour change and a number of the bacteria.

15. A method for detecting bacteria, comprising:

adding a sample, to be analysed, to an analysis reagent held in a reaction container, wherein the reaction container is appropriately sterilised and maintained at a temperature of about 25 to about 45 ° C.;

determining a time for a colour change of the analysis reagent to occur in response to adding the sample to the analysis reagent and determining a concentration of the bacteria in the sample at least partially based on the time for the colour change;

wherein the analysis reagent includes an aqueous solution including:

about 1 to about 100 g/l of at least one source of amino acids selected from the group consisting of meat peptone, vegetable peptone, casein hydrolysate, tryptose, tryptone, and yeast extract;

about 0 to about 200 g/l of a buffer system suitable for maintaining the overall pH between about 5.5 and about 8.5;

about 0.03 to about 3 g/l of a redox indicator having a potential between about −250 and about +250 mV;

a pH indicator with a colour change interval between a pH of about 5.5 and a pH of about 8.5;

about 0 to about 200 g/l of a selective agent for the detection of a specific class of bacteria; and an organic liquid compound that is not miscible with water and has a density less than water.

\* \* \* \* \*